(12) United States Patent
Liang et al.

(10) Patent No.: US 9,152,926 B2
(45) Date of Patent: *Oct. 6, 2015

(54) SYSTEMS, METHODS, AND MEDIA FOR UPDATING A CLASSIFIER

(71) Applicant: Arizona Board of Regents, for and on Behalf of, Arizona State University, Scottsdale, AZ (US)

(72) Inventors: Jianming Liang, Phoenix, AZ (US); Hong Wu, Tempe, AZ (US); Wenzhe Xue, Chandler, AZ (US); Nima Tajbakhsh, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/376,181

(22) PCT Filed: Feb. 4, 2013

(86) PCT No.: PCT/US2013/024675
§ 371 (c)(1),
(2) Date: Aug. 1, 2014

(87) PCT Pub. No.: WO2013/116865
PCT Pub. Date: Aug. 8, 2013

(65) Prior Publication Data
US 2015/0012472 A1    Jan. 8, 2015

Related U.S. Application Data

(60) Provisional application No. 61/594,240, filed on Feb. 2, 2012.

(51) Int. Cl.
*G06N 99/00* (2010.01)
*G06N 5/04* (2006.01)
(Continued)

(52) U.S. Cl.
CPC ............ *G06N 99/005* (2013.01); *G06K 9/6256*
(2013.01); *G06K 9/6267* (2013.01); *G06N 5/043* (2013.01); *G06N 5/046* (2013.01); *G06F 19/321* (2013.01); *G06F 19/345* (2013.01)

(58) Field of Classification Search
CPC .................................................... G06N 99/005
See application file for complete search history.

(56) References Cited

U.S. PATENT DOCUMENTS 7,526,101 B2    4/2009    Avidan
7,840,061 B2    11/2010   Porikli et al.
(Continued)

OTHER PUBLICATIONS

"Deep Vein Thrombosis Overview", Technical Report, Society of Intenventional Radiology, last accessed Sep. 17, 2014, pp. 1-3, available at: http://www.sirweb.org/patients/deep-vein-thrombosis/.

(Continued)

*Primary Examiner* — Jeffrey A Gaffin
*Assistant Examiner* — Ola Olude Afolabi
(74) *Attorney, Agent, or Firm* — Byrne Poh LLP

(57) ABSTRACT

Systems, methods, and media for updating a classifier are provided, in some embodiments, systems for updating a classifier are provided, the systems comprising: a hardware processor that is configured to: receive a sample; for each of a first plurality of weak learners, classify the sample using the weak learner, determine an outcome of the classification, and determine an up-dated error rate of the weak learner based on the outcome of the classification and at least one of: (i) a count of positive samples used to update the classifier, and (ii) a count of negative samples used to update the classifier; select a first weak learner from the first plurality of weak learners based on the updated error rate of the first weak learner; and update tire classifier based on the first weak learner.

42 Claims, 10 Drawing Sheets

(51) Int. Cl.
 G06K 9/62 (2006.01)
 G06F 19/00 (2011.01)

(56) References Cited

U.S. PATENT DOCUMENTS

| | | |
|---|---|---|
| 2003/0199762 A1 | 10/2003 | Fritz et al. |
| 2005/0220336 A1 | 10/2005 | Sabe et al. |
| 2005/0228276 A1 | 10/2005 | He et al. |
| 2007/0280530 A1 | 12/2007 | Fung et al. |
| 2008/0009733 A1 | 1/2008 | Saksena |
| 2008/0154565 A1 | 6/2008 | Florin et al. |
| 2008/0171939 A1 | 7/2008 | Ishihara |
| 2008/0192887 A1 | 8/2008 | Weese et al. |
| 2008/0240532 A1 | 10/2008 | Carneiro et al. |
| 2008/0260230 A1 | 10/2008 | Gotardo et al. |
| 2009/0034816 A1 | 2/2009 | Ghanem et al. |
| 2009/0060307 A1 | 3/2009 | Ghanem et al. |
| 2009/0175515 A1 | 7/2009 | Schummers |
| 2009/0252394 A1 | 10/2009 | Liang et al. |
| 2010/0046815 A1 | 2/2010 | Von Berg et al. |
| 2010/0061601 A1 | 3/2010 | Abramoff et al. |
| 2010/0098308 A1 | 4/2010 | Lakare et al. |
| 2010/0113930 A1 | 5/2010 | Miyachi |
| 2010/0177944 A1 | 7/2010 | Madabhushi et al. |
| 2011/0270089 A1 | 11/2011 | Vezina |
| 2011/0293157 A1 | 12/2011 | Ye et al. |
| 2012/0089545 A1 | 4/2012 | Mei et al. |
| 2012/0106815 A1 | 5/2012 | Yang et al. |
| 2012/0274755 A1 | 11/2012 | Sinha et al. |
| 2013/0070997 A1* | 3/2013 | Tajbakhsh et al. ............ 382/131 |

OTHER PUBLICATIONS

Alonso-Martnez, J.L., et al., "Delay and misdiagnosis in sub-massive and non-massive acute pulmonary embolism", In European Journal of Internal Medicine, vol. 21, No. 4, Aug. 2010, pp. 278-282.
Araoz, P.A., et al., "Helical ct pulmonary angiography predictors of in-hospital morbidity and mortality in patients with acute pulmonary embolism", In Journal of Thoracic Imaging, vol. 18, Oct. 2003, pp. 207-216.
Bi, J. and Liang, J., "Multiple instance learning of pulmonary embolism detection with geodesic distance along vascular structure", In Proceedings of IEEE Computer Society Conference on Computer Vision and Pattern Recognition (CVPR) Jun. 17-22, 2007, Minneapolis, MN USA, pp. 1-8.
Bottiger, S.W., et al., "Inhaled nitric oxide selectively decreases pulmonary artery pressure and pulmonary vascular resistance following acute massive pulmonary microembotism in piglets," In Chest, vol. 110, No. 4, Oct. 1996, pp. 1041-1047.
Bouma, H., "Vessel-Diameter Quantification and Embolus Detection in CTA Images." Ph.D. Thesis, Eindhoven University of Technology, PnntPartners, Ipskamp, The Netherlands, Apr. 2008, pp. 9-133.
Bouma, H., et al, "Automatic Detection of Pulmonary Embolism in CTA Images", in IEEE Transactions on Medical Imaging, vol. 28. No. 8, Aug. 2009, pp. 1223-1230.
Bourdev, L. and Brandt, J., et al., "Robust Object Defection via Soft Cascade", In Proceedings of the 2005 IEEE Conference on Computer Vision and Pattern Recognition (CVPR'05), Washington, DC, USA, Jun. 2005. pp. 236-243.
Chartrand-Lefebvre, C., "Computed tomography angiography in the diagnosis of pulmonary embolism: Interobserver agreement", In American Journal of Emergency Medicine, Jan. 27, 2011, pp. 118-119.
Cho, E.J., et al., "Right ventricular free wall circumferential strain reflects graded elevation in acute right ventricular afterload". In Am J Physiol Heart Circ Physiol., Feb. 2009, vol. 296, No. 2, pp. 818-824.
Collomb, J., et al., "Severity Assessment of Acute Pulmonary Embolism: Evaluation using Helical CT," In European Radioiogy, vol. 13, No. 7, 2003, pp. 1508-1514.
Costantino, C., et al., "Interobserver agreement in computer tomography readings for pulmonary embolism", In American Journal of Emergency Medicine, Jan. 27, 2011, pp. 119.
Costantino, G., et al., "Interobserver agreement in computer tomography readings for pulmonary embolism" In American Journal of Emergency Medicine, vol. 27, No. 9, Nov. 2009, pp. 1109-1111.
Craig, J.J., "Introduction to Robotics: Mechanics and Control", 3rd edition, Prentice Hall, Aug. 6, 2004, pp. 1-385.
Criminisi, A., et al., "Regression Forests for Efficient Anatomy Defection and Localization in CT Studies", In Proceedings of the International Workshop on Medical Computer Vision, Beijing, CN, Sep. 2010, pp. 106-117.
Crow, F. C., "Summed-Area Tables for Texture Mapping". In Computer Graphics, vol. 18, No. 3 Jul. 1984, pp. 207-212.
Dias-Junior, C.A., "The effect of sildenafil on pulmonary embolism-induced oxidative stress and pulmonary hypertension", In Anesthesia & Analgesia, vol. 101, No. 1, Jul. 2005, pp. 115-120.
Dinesh, M.S., et al. "Adaptive Contrast-Based Computer Aided Detection for Pulmonary Embolism", In Proceedings of the SPIE International Society Conference for Optimal Engineering, Mar. 2009. vol. 7260, No. 726010, pp. 1-8.
Dollar, P., et al., "Multiple Component Learning for Object Detection", In Proceedings of the 10th European Conference on Computer Vision Part II (ECCV '08): Marseille, FR, Oct. 12-18, 2008, pp. 211-224.
Dousset, M., et al., "Principles and performance of virtual CT and MIRA intraluminal endoscopy", In Virtual Endoscopy, Springer, Nov. 2002, pp. 1-19.
Frangi, A.F., et al., "Multiscale vessel enhancement filtering", In Medical Image Computing and Computer-Assisted Intervention, Oct. 11-13, 1998, pp. 130-137.
Freund, Y. and Schapire, R.E., "A Decision-Theoretic Generalization of On-Line Learning and an Application to Boosting", In Journal of Computer and System Sciences, vol. 55, No. 1, Aug. 1997, pp. 119-139.
Freund, Y., and Schapire, R.E., "A Short Introduction to Boosting", In Journal of Japanese Society for Artificial Intelligence, vol. 14, No. 5, Sep. 1999. pp. 771-780.
Gaison, S.,K., "The surgeon general's call to action to prevent deep vein thrombosis and pulmonary embolism", Technical Report, U.S. Public Health Services, Sep. 15, 2008, pp. 1-35.
Ghaye, B., et al., "Can CT Pulmonary Angiography Allow Assessment of Severity and Prognosis in Patients Presenting with Pulmonary Embolism? What the Radiologist Needs to Know," In RadioGraphics, vol. 26. Jan. 2006, pp. 23-29.
Ghaye, B., et al., "Severe pulmonary embolism: pulmonary artery clot load scores and cardiovascular parameters as predictors of mortality," In Radiology, vol. 239, 2006, pp. 884-891.
Godec, M., et al., "On-line Random Naive Bayes for Tracking", In Proceedings of the 20th International Conference (ICPR '10), Istanbul, TR, Aug. 23-26, 2010, pp. 3545-3548.
Goldstein, H., "Classical Mechanics", 2nd Edition, Jul. 1980, pp. 1-2.
Grabner, H. and Bischof, H., "On-line Boosting and Vision", In Proceedings of the IEEE Computer Society Conference on Computer Vision and Pattern Recognition (CVPR '06), New York, NY, USA, Jun. 17-22, 2006, pp. 260-267.
Grbovic, M. and Vucetic, S., "Tracking Concept Change with Incremental Boosting by Minimization of the Evolving Exponential Loss", In Proceedings of the European Conference on Machine Learning and Knowledge Discovery in Databases, Athens, GR, Sep. 5-9, 2011, pp. 516-532.
Grifoni, S.,"Short-term clinical outcome of patients with acute pulmonary embolism, normal blood pressure, and echocardiographic right ventricular dysfunction," In Circulation, vol. 101, No. 24, Jun. 2000, pp. 2817-2822.
Groth. M., et al., "Correlation of right ventricular dysfunction parameters and pulmonary vascular obstruction score in acute pulmonary embolism in a porcine model", In Emergency Radiology, Sep. 2010, pp. 367-374.
He, H., et al., "Incremental Learning from Stream Data," In IEEE Transactions on Neural Networks, vol. 22, No. 12, Dec. 2011, pp. 1901-1914.
International Patent Application No. PCT/US2013/024677, filed Feb. 4, 2013.
International Preliminary Report on Patentability dated Aug. 22, 2013 in International Patent Application No. PCT/UA2012/024925.

(56) References Cited

OTHER PUBLICATIONS

International Preliminary Report on Patentability in International Application No. PCT/US2012/024907, filed Feb. 13, 2012, mailed Aug. 22, 2013.
International Search Report in International Patent Application No. PCT/US2012/024925, filed Feb. 13, 2012, mailed Jun. 19, 2012.
International Search Report in International Patent Application No. PCT/US2013/024675, filed Feb. 4, 2013, mailed Apr. 16, 2013.
International Search Report in International Patent Application No. PCT/US2013/024677, filed Feb. 4, 2013, mailed Apr. 15, 2013.
Jardin, F., et al., "Echocardiographic pattern of acute cor pulmonale," In Chest, vol. 111, No. 1, Jan. 1997, pp. 209-217.
Kanitsar, A., et al., "CPR—Curved Planer Reformation", In Proceedings of IEEE Visualization. Nov. 1, 2002, pp. 37-44.
Kass, M., et al., "Snakes: Active contour models." In International Journal of Computer Vision, vol. 1. No. 4, Jan. 1988, pp. 321-331.
Kim, T.K., et al., "Online Multiple Classier Boosting for Object Tracking". In Proceedings of the 2010 IEEE Computer Society Conference on Computer vision and Pattern Recognition Workshops (CVPRW '10), San Francisco, CA, USA, Jun. 13-18, 2010, pp. 1-6.
Kiraly, A.P., et al., "Cartwheel projections of segmented pulmonary vasculature for the detection of pulmonary embolism", In Medical Imaging: Visualization, Image-Guided Procedures, and Display, Proc. SPIE 5744, Apr. 12, 2005, pp. 69-78.
Knutsson, H., "Representing Local Structure using Tensors", In Proceedings of the 6th Scandinavian Conference on Image Analysis, Oulu, Finland, Jun. 1989, pp. 244-251.
Kothe, U., "Edge and Junction Detection with an Improved Structure Tensor", In Proceedings of the 25th DAGM Symposium on Pattern Recognition, Magdeburg, DE, Sep. 10-12, 2003, pp. 25-32.
Kurkure, U., et al., "Automated Segmentation of Thoracic Aorta in Non-Contrast CT Images", In Proceedings of the 5th International Symposium on Biomedical Imaging: From Nano to Macro (ISBI '08). Paris, FR, May 14-17, 2008, pp. 29-32.
Leistner. C., et al., "On Robustness of On-line Boosting—A Competitive Study", In Proceedings of the 2009 IEEE 12th International Conference on Computer Vision Workshops (ICCVW '09), Kyoto, JP, Sep. 27-Oct. 4, 2009, pp. 1362-1369.
Levenberg, K., "A method for the solution of certain non-linear problems in least squares", In Quarterly Journal of Applied Mathmatics. vol. 2, 1944. pp. 164-168.
Liang, J. and Bi, J., "Computer Aided Detection of Pulmonary Embolism with Tobogganing and Multiple Instance Classification in CT Pulmonary Angiography", In Proceedings of the 20th Intl Conference of Information Processing in Medical Imaging Kerkrade, NL, Jul. 2-6, 2007, pp. 630-641.
Liang, J, and Bi, J., "Local Characteristic Features for Computer-Aided Detection of Pulmonary Embolism in CT Angiography", In Proceedings of the First Workshop on Pulmonary Image Analysis. New York, NY, US, Sep. 6, 2008. pp. 263-272.
Liang, J., et al., "United Snakes". In Medical Image Analysis, vol. 10 No. 2, Apr. 2006, vol. 215-233.
Liu, D., et al., "Search strategies for multiple landmark detection by submodular maximization", IEEE Conference on Computer Vision and Pattern Recognition, Jun. 3-8, 2010, San Francisco, CA, USA, pp. 2831-2838.
Liu, X. and Yu, T., "Gradient Feature Selection for Online Boosting", In Proceedings of the IEEE 11th International Conference on Computer Vision (ICCV '07), Rio de Janeiro, BR, Oct. 14-21, 2007, pp. 1-8.
Lorenz, C., et al., "Multi-scale line segmentation with automatic estimation of width, contrast and tangential direction in 2-D and 3-D medical images", In Proceedings of the 1st Joint Conference on Computer Vision, Virtual Reality and Robotics in Medicine and Medical Robotics and Computer-Assisted Surgery, London. UK, Springer, 1997, pp. 233-242.
Mansencal, N., "Comparison of different echocardiographic indexes secondary to right ventricular obstruction in acute pulmonary embolism," In The American Journal of Cardiology, vol. 92, No. 1, Jul. 2003, pp. 116-119.

Marquardt, D.W., "An Algorithm for Least-Squares Estimation of Nonlinear Parameters," In SIAM Journal on Applied Mathematics, vol. 11 No. 2, Jun. 1963, pp. 431-441.
Mastora, I., "Severity of acute pulmonary embolism: evaluation of a new spiral ct angiographic score in correlation with echocardiographic data". In European Radiology, vol. 13, Jan. 2003, pp. 29-36.
Masutani, Y., et al., "Computerized Detection of Pulmonary Embolism in Spiral CT Angiography Based on Volumetric Image Analysis", In IEEE Transactions on Medical Imaging, vol. 21. No. 12, Dec. 2002, pp. 1517-1523.
McConnell, M.V., et al., "Regional right ventricular dysfunction detected by echocardiography in acute pulmonary embolism," In The American Journal of Cardiology, vol. 78 No. 4, Aug. 1996. pp. 469-473.
Office Action dated Jul. 17, 2014 in U.S. Appl. No. 13/621,837.
Office Action dated Aug. 16, 2013 in U.S. Appl. No. 13/964,800.
Office Action dated Aug. 23, 2013 in U.S. Appl. No. 13/984,808.
Office Action dated Oct. 7, 2013 in U.S. Appl. No. 14/023,380.
Office Action dated Sep. 18, 2013 in European Patent Application No. 12744949.4.
Ouellette, D.R., et al., "Pulmonary Embolism", Medscape.com, last updated Sep. 4, 2014, available at: http://emedicine.medscape.com/article/300901-overview#showall, pp. 1-24.
Oza, N. C. and Russell, S., "Online, Bagging and Boosting", In 8th International Workshop on Artificial Intelligence and Statistics, Key West, FL, USA, Jan. 2001, pp. 105-112.
Parag, T., et al., "Boosting Adaptive Linear Weak Classifiers for Online Learning and Tracking". In Proceedings of the IEEE Conference on Computer Vision and Recognition (CVPR '08), Anchorage, AK, USA. Jun. 23-28, 2008, pp. 1-8.
Parikh, D. and Polikar, R., "An Ensemble-Based Incremental Learning Approach to Data Fusion", In IEEE Transactions on Systems, Man, Cybernetics, Part B: Cybernetics, vol. 37, No. 2, Apr. 2007, pp. 437-450.
Pelossof, R., et al., "Online Coordinate Boosting", In Proceedings of the 2009 IEEE 12th International Conference on Computer Vision Workshops, (ICCVW '09), Kyoto, JP. Sep. 27-Oct. 4, 2009, pp. 1354-1361.
Pham, M. and Cham, T., "Detection with Multi-exit Asymmetric Boosting", In Proceedings of the IEEE Conference on Computer Vision and Pattern Recognition (CVPR '06), Anchorage, AK, USA, Jun. 23-26, 2008, pp. 1-8.
Pham, M. and Cham, T., "Fast Training and Selection of Haar Features Using Statistics in Boosting-Based Face Detection", In Proceedings of the IEEE 11th International Conference on Computer Vision (ICCV '07), Rio de Janeiro, BR, Oct. 14-21, 2007, pp. 1-7.
Pham, M. and Cham, T., "Online Learning Asymmetric Boosted Classifiers for Object Detection", In Proceedings of the IEEE Conference on Computer Vision and Recogition (CVPR '07), Minneapolis, MN, USA, Jun. 17-22, 2007. pp. 1-8.
Ribeiro, A., et al., "Echocardiography doppler in pulmonary embolism: Right ventricular dysfunction as a predictor of mortality rate," In American Heart Journal, vol. 134, No. 3, Mar. 1997, pp. 479-487.
Sato, Y, et al., "3-D multi-scale line filter for segmentation and visualization of curvilinear structures in medical images". In Proceedings of the 1st Joint Conference on Computer Vision, Virtual Reality and Robotics in Medicine and Medical Robotics, London, UK, Mar. 19-22, 1997, pp. 213-222.
Schapire. R. E. and Singer, Y., "BoosTexter: A Boosting-Based System for Text Categorization", In Machine Learning, vol. 39, No. 2, May 1, 2000, pp. 135-168.
Schapire, R. E., "Theoretical Views of Boosting and Applications", In Algorithmic Learning Theory, Lecture Notes in Computer Science, vol. 1720. Dec. 1999, pp. 13-25.
Sebbe, R., "Computer-aided Diagnosis of Pulmonary Embolism in Opacified CT Images", Ph.D. Dissertation, Faculte Polytechnique de Mons, Univeraitaires de Louvain, Belgium, Feb. 20, 2007, pp, 1-124.
Simon, M., et al., "Paddie-wheel CT display of pulmonary arteries and other lung structures: a new imaging approach". In American Journal of Roentgenology. Jul. 2001, pp. 195-196.

(56) References Cited

OTHER PUBLICATIONS

Simon, M., et al., "Paddle-wheel multislice helical CT display of pulmonary vessels and other lung structures", In Radiologic Clinics of North America. May 2003, pp. 617-626.
Stein, P.D. and Hull, R.D., "Multidetector computed tomography for the diagnosis of acute pulmonary embolism", In Current Opinion Pulmonary Medicine, Sep. 2007, pp. 384-388.
Stein, P.D. and Matta, F., "Acute Pulmonary Embolism", In Current Problems in Cardiology, vol. 35, No. 7, Jul. 2010, pp. 314-376.
Sternig, S., et al., "Transient Boost: On-line Boosting with Transient Data", In Proceedings of the 2010 IEEE Computer Society Conference on Computer Vision and Pattern Recognition Workshops (CVPRW '10): San Francisco, CA, USA, Jun. 13-18, 2010, pp. 22-27.
Tajbakhsh, N., et al., "Motion analysis of right ventricular dysfunction under mild and moderate pressure overload caused by acute pulmonary embolism", In Ultrasound in Medicine and Biology, vol. 39, No. 11, Nov. 2013, pp. 2066-2074.
Tajbakhsh, N., et al., "Shape-based analysis of right ventricular dysfunction associated with acute pulmonary embolism", In SPIE Medical Imaging, vol. 8317, Mar. 2012, pp. 83170G-83170G.
Takamura, T., et al., "Reversible left ventricular regional non-uniformity quantified by speckie-tracking displacement and strain imaging in patients with acute pulmonary embolism," In Journal of the American Society of Echocardiography, vol. 24, No. 7, Apr. 2011, pp. 792-802.
Torbicki, A., et al., "Guidelines on the diagnosis and management of acute pulmonary embolism of the European Society of Cardiology", In Eur Heart J., vol. 29, No. 18, Sep. 2008, pp. 2276-2315.
Vaidehi, V., et al., "Multiclass Object Detection System in Imaging Sensor Network Using Haar-like Features and Joint-Boosting Algorithm", In Proceedings of the 2011 International Conference on Recent Trends in Information Technology (ICRTIT '11), Chennai, Tamil Nadu, IN, Jun. 3-5, 2011, pp. 1011-1015.
Viola, P. and Jones M., "Fast and Robust Classification Using Asymmetric AdaBoost and a Detector Cascade", In Proceedings of the Annual Conference on Neural Information Processing Systems, Vancouver, BC, CA, Dec. 3-8, 2001, pp. 1311-1318.
Viola, P. and Jones, M., "Rapid Object Detection using a Boosted Cascade of Simple Features", In Proceedings of the IEEE Computer Society Conference on Computer Vision and Pattern Recognition, Kauai, HI, USA. Dec. 8-14, 2001, pp. 511-518.
Written Opinion in International Patent Application No. PCT/US2012/024925, filed Feb. 13, 2012, mailed Jun. 19, 2012.
Written Opinion in International Patent Application No. PCT/US2013/024675, filed Feb. 4, 2013, mailed Apr. 16, 2013.
Written Opinion in International Patent Application No. PCT/US2013/024677, filed Feb. 4, 2013, mailed Apr. 15, 2013.
Wu, B, and Nevatia, R., "Improving Part Based Object Detection by Unsupervised, Online Boosting", In Proceedings of the IEEE Conference on Computer Vision and Pattern Recognition (CVPR '07), Minneapolis, MN, USA, Jun. 17-22, 2007, pp. 1-8.
Wu, H., et al. "Self-Adaptive Asymmetric On-line Boosting for Detecting Anatomical Structures", In SPIE Medical Imaging, vol. 8315, Feb. 2012, pp. 831539-831539.
Wu, H., et al., "Machine Learning based Automatic Detection of Pulmonary Trunk", In Proceedings of the SPIE Conference on Medical Imaging 2011: Computer-Aided Diagnosis, Lake Buena Vista, FL, USA, Feb. 12, 2011, vol. 7963, pp. 1-6.
Zheng, Y., et al., "Automatic Aorta Segmentation and Valve Landmark Detection in C-Arm CT: Application to Aortic Valve Implantation", In IEEE Transactions on Medical Imaging, vol. 31, No. 12, Dec. 2012, pp. 2307-2321.
Zheng, V., et al., "Fast Automatic Heart Chamber Segmentation from 3D CT Data Using Marginal Space Learning and Steerable Features", In Proceedings of the IEEE 11th International Conference on Computer Vision (ICCV '07), Rio de Janeiro, BR, Oct. 14-21, 2007, pp. 1-8.
Zhou, C., et al., "Automatic Pulmonary Vessel Segmentation in 3D Computed Tomographic Pulmonary Angiographic (CTPA) Images", In Proceedings of the SPIE 6144, Medical Imaging: Image Processing, Mar. 15, 2006, pp. Q1-Q7.
Zhou, S. K., et al., "A Boosting Regression Approach to Medical Anatomy Detection", In Proceedings of the IEEE Conference on Computer Vision and Pattern Recognition (CVPR '07), Minneapolis, MN, USA, Jun. 17-22, 2007, pp. 1-8.
Zou, X. et al., "Anatomy-Based Automatic Detection and Segmentation of Major Vessels in Thoracic CTA Images", In Computerized Medical Imaging and Graphics, vol. 30. No. 5, Jul. 2006, pp. 299-313.
Howard, G., et al., "For the ARIC Investigators: Carotid Artery Intimal-Medial Thickness Distribution in General Populations as Evaluated by B-Mode Ultrasound", In Stroke, vol. 24, No. 9, Sep. 1993, pp. 1297-1304.
Hurst, R., et al., "Clinical Use of Carotid Intima-Media Thickness: Review of the Literature", In Journal of the American Society of Echocardiography, vol. 20, No. 7, Jul. 2007, pp. 907-914.
Li, S., et al., "Childhood Cardiovascular Risk Factors and Carotid Vascular Changes in Adulthood: the Bogalusa Heart Study", in the Journal of the American Medical Association (JAMA), vol. 290, No. 17, Nov. 2003, pp. 2271-2276.
Office Action dated Jan. 29, 2015 in U.S. Appl. No. 13/621,837.
Stein, J., et al., "A Semiautomated Ultrasound Border Detection Program that Facilitates Clinical Measurement of Ultrasound Carotid Intima-Media Thickness", in the Journal of the American Society of Echocardiography, vol. 18, No. 3, Mar. 2005, pp. 244-251.
Stein, J., et al., "Use of Carotid Ultrasound to Identify Subclinical Vascular Disease & Evaluate Cardiovascular Disease Risk: A Consensus Statement from the American Society of Echocardiography Carotid Intima-Media Thickness Task Force", In the Journal of Am. Soc. of Echocardiography, vol. 21, No. 2, Feb. 2008, pp. 93-111.
Stein, J., et al., "Vascular Age: Integrating Carotid Intima-Media Thickness Measurements with Global Coronary Risk Assessment", In Clinical Cardiology, vol. 27, No. 7, Jul. 2004, pp. 388-392.
Wu, H., "Offline and Online Adaboost for Detecting Anatomical Structures", Thesis Paper, Arizona State University, Aug. 2011, pp. 1-66.
Frangi, A.F., et al., "Model-Based Quantitation of 3-D Magnetic Resonance Angiographic Images", In IEEE Transactions on Medical Imaging, vol. 18, No. 10, Oct. 1999, pp. 946-956.
Office Action dated Apr. 24, 2015 in U.S. Appl. No. 14/023,380.

* cited by examiner

Require: training example $(x,y), y \in \{-1,+1\}$
Require: weights $\lambda_{n,m}^{TP}, \lambda_{n,m}^{FP}, \lambda_{n,m}^{TN}, \lambda_{n,m}^{FN}$ (initialized with 1)
Require: sample's importance weight $\lambda$ (initialized with 1)
Require: $num_{pos}$ and $num_{neg}$ are the numbers
of positive and negative samples been exposed to SAAOB (initialized with 1)

for m = 1,2,...,M do // update all the weak learners
$h_m^{weak}$ = update($h_m^{weak}$, (x,y))
end for

FIG. 7A for n = 1,2,...,N do // update the weak learner parameters in all selectors
  for m = 1,2,...,M do // update the weak learner parameters in selector n
    // estimate errors
    if $h_{n,m}^{weak}(x) = +1$ and $y = +1$ then // true positive
      $\lambda_{n,m}^{TP} = \lambda_{n,m}^{TP} + \lambda$
    else if $h_{n,m}^{weak}(x) = +1$ and $y = -1$ then // false positive
      $\lambda_{n,m}^{FP} = \lambda_{n,m}^{FP} + \lambda$
    else if $h_{n,m}^{weak}(x) = -1$ and $y = -1$ then // true negative
      $\lambda_{n,m}^{TN} = \lambda_{n,m}^{TN} + \lambda$
    else if $h_{n,m}^{weak}(x) = -1$ and $y = +1$ then // false negative
      $\lambda_{n,m}^{FN} = \lambda_{n,m}^{FN} + \lambda$
    end if
    // asymmetric loss criterion $$\mathcal{E}_{n,m} = \frac{1}{1+2\epsilon}\left[\left(\frac{numneg}{numpos+numneg}+\epsilon\right)\frac{\lambda_{n,m}^{FP}}{\lambda_{n,m}^{TP}+\lambda_{n,m}^{FP}+\lambda_{n,m}^{TN}+\lambda_{n,m}^{FN}} + \left(\frac{numpos}{numpos+numneg}+\epsilon\right)\frac{\lambda_{n,m}^{FN}}{\lambda_{n,m}^{TP}+\lambda_{n,m}^{FP}+\lambda_{n,m}^{TN}+\lambda_{n,m}^{FN}}\right]$$

end for

FIG. 7B

// choose the best weak learner and get the parameters for selector $n$ $m_{best} = argmin_m(e_{n,m}); h_n^{sel} = h_{n,m_{best}}^{weak}; \mathcal{E}_n = \mathcal{E}_{n,m_{best}}; \alpha_n = \log \frac{1-e_n}{e_n}$ $\lambda_n^{TP} = \lambda_{n,m_{best}}^{TP}; \lambda_n^{FP} = \lambda_{n,m_{best}}^{FP}; \lambda_n^{TN} = \lambda_{n,m_{best}}^{TN}; \lambda_n^{FN} = \lambda_{n,m_{best}}^{FN}$ //update sample's importance weight if $h_n^{sel}(x) = +1$ and $y = +1$ then // true positive $\lambda = \frac{1}{2}\lambda \frac{num^{pos}+num^{neg}}{\lambda_n^{TP}+\lambda_n^{FP}+\lambda_n^{TN}+\lambda_n^{FN}} \frac{\lambda_n^{TP}+\lambda_n^{FP}}{\lambda_n^{TP}}$ else if $h_n^{sel}(x) = +1$ and $y = -1$ then // false positive $\lambda = \frac{1}{2}\lambda \frac{num^{pos}+num^{neg}}{\lambda_n^{TP}+\lambda_n^{FP}+\lambda_n^{TN}+\lambda_n^{FN}} \frac{\lambda_n^{TP}+\lambda_n^{FP}}{\lambda_n^{FP}}$ else if $h_n^{sel}(x) = -1$ and $y = -1$ then // true negative $\lambda = \frac{1}{2}\lambda \frac{num^{pos}+num^{neg}}{\lambda_n^{TP}+\lambda_n^{FP}+\lambda_n^{TN}+\lambda_n^{FN}} \frac{\lambda_n^{TN}+\lambda_n^{FN}}{\lambda_n^{TN}}$ else if $h_n^{sel}(x) = -1$ and $y = +1$ then // false negative $\lambda = \frac{1}{2}\lambda \frac{num^{pos}+num^{neg}}{\lambda_n^{TP}+\lambda_n^{FP}+\lambda_n^{TN}+\lambda_n^{FN}} \frac{\lambda_n^{TN}+\lambda_n^{FN}}{\lambda_n^{FN}}$ end if
end for

$h^{strong}(x) = sign(\sum_{n=1}^{N} \alpha_n h_n^{sel}(x))$ // strong learner

FIG. 7C

SYSTEMS, METHODS, AND MEDIA FOR UPDATING A CLASSIFIER

CROSS REFERENCE TO RELATED APPLICATION

This application claims the benefit of U.S. Provisional Patent Application No. 61/594,240, filed Feb. 2, 2012, which is hereby incorporated by reference herein in its entirety.

TECHNICAL FIELD

The disclosed subject matter relates to systems, methods, and media for updating a classifier.

BACKGROUND

Automatic detection of certain content in images and/or other forms of data is of ever-increasing importance for machine vision, security, computer-aided diagnosis and other applications. For example, automated detection of anatomic structures is an important functionality for navigating through large 3D image datasets and supporting computer-aided diagnosis (CAD).

A classifier is a mechanism that can be used to perform automatic detection in such applications. Once trained, a classifier can indicate whether an image includes a certain object, such as an anatomic structure. Based on the amount of training, a classifier can exhibit a better or worse performance. With an on-line classifier, training may be performed during normal use of the classifier. Because of this ability to train during normal use, and hence continually improve performance while being used, on-line classifiers are increasing in popularity.

However, current on-line classifiers lack adaptations for dealing with training data sets where an imbalance exists between the proportions of true-positive, true-negative, false-positive, and false-negative samples. Furthermore, current on-line classifiers are unable to adapt to shifts in the proportions of positive and negative samples that occur as the sizes of training data sets expand over time.

Accordingly, new mechanisms for updating a classifier are desirable.

SUMMARY

Systems, methods, and media for updating a classifier are provided. In accordance with some embodiments, systems for updating a classifier are provided. The systems include a hardware processor that is configured to: receive a sample; for each of a first plurality of weak learners, classify the sample using the weak learner, determine an outcome of the classification, and determine an updated error rate of the weak learner based on the outcome of the classification and at least one of (i) a count of positive samples used to update the classifier, and (ii) a count of negative samples used to update the classifier; select a first weak learner from the first plurality of weak learners based on the updated error rate of the first weak learner; and update the classifier based on the first weak learner.

In accordance with some embodiments, systems for updating a classifier are provided. The systems include a hardware processor that is configured to: receive a sample; assign a first importance weight to the sample based on a count of samples used to update the classifier; for each of a first plurality of weak learners, classify the sample using the weak learner, determine an outcome of the classification, and determine an updated error rate of the weak learner based on the outcome of the classification and the first importance weight; select a first weak learner from the first plurality of weak learners based on the updated error rate of the first weak learner; and update the classifier based on the first weak learner.

In accordance with some embodiments of the disclosed subject matter, methods for updating a classifier are provided. The methods comprising: receiving a sample; for each of a first plurality of weak learners, classifying the sample using the weak learner, determining an outcome of the classification, and determining, by a hardware processor, an updated error rate of the weak learner based on the outcome of the classification and at least one of: (i) a count of positive samples used to update the classifier, and (ii) a count of negative samples used to update the classifier; selecting a first weak learner from the first plurality of weak learners based on the updated error rate of the first weak learner; and updating the classifier based on the first weak learner.

In accordance with embodiments of the disclosed subject matter, methods for updating a classifier are provided. The methods comprising: receiving a sample; assigning a first importance weight to the sample based on a count of samples used to update the classifier; for each of a first plurality of weak learners, classifying the sample using the weak learner, determining an outcome of the classification, and determining, by a hardware processor, an updated error rate of the weak learner based on the outcome of the classification and the first importance weight; selecting a first weak learner from the first plurality based on the updated error rate of the first weak learner; and updating the classifier based on the first weak learner.

In accordance with embodiments of the disclosed subject matter, non-transitory computer-readable media are provided that contain computer-executable instructions that, when executed by a processor, cause the processor to perform a method for updating a classifier. In some embodiments, the method comprises: receiving a sample; for each of a first plurality of weak learners, classifying the sample using the weak learner, determining an outcome of the classification, and determining an updated error rate of the weak learner based on the outcome of the classification and at least one of: (i) a count of positive samples used to update the classifier, and (ii) a count of negative samples used to update the classifier; selecting a first weak learner from the first plurality of weak learners based on the updated error rate of the first weak learner; and updating the classifier based on the first weak learner.

In accordance with embodiments of the disclosed subject matter, non-transitory computer-readable media are provided that contain computer-executable instructions that, when executed by a processor, cause the processor to perform a method for updating a classifier. In some embodiments, the method comprises: receiving a sample; assigning a first importance weight to the sample based on a count of samples used to update the classifier; for each of a first plurality of weak learners, classifying the sample using the weak learner, determining an outcome of the classification, and determining, an updated error rate of the weak learner based on the outcome of the classification and the first importance weight; selecting a first weak learner from the first plurality of weak learners based on the updated error rate of the first weak learner; and updating the classifier based on the first weak learner.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIG. 7 is an example of pseudo-code for a process for updating a classifier in accordance with some embodiments of the disclosed subject matter.

DETAILED DESCRIPTION

Figure 1:
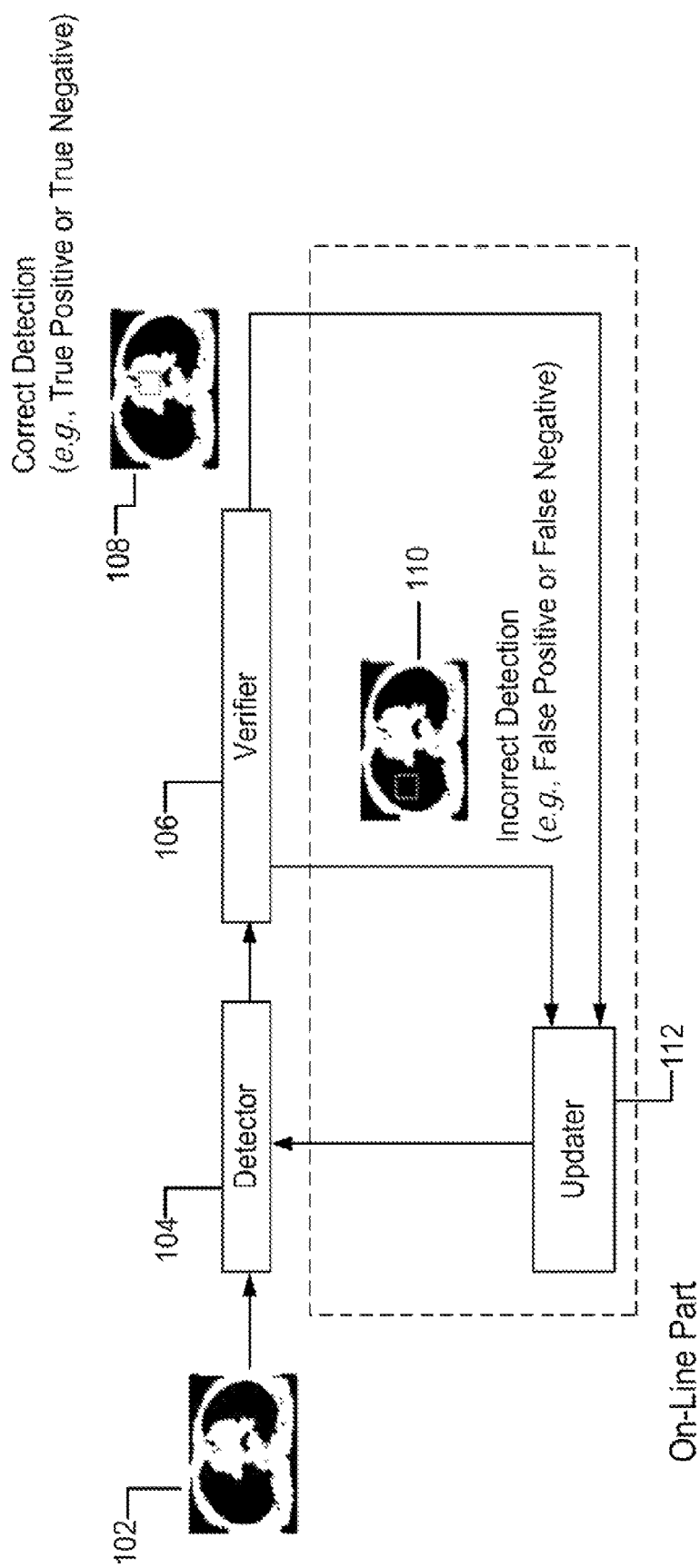
FIG. 1 is a block diagram of an example of a system for updating a classifier in accordance with some embodiments of the disclosed subject matter.

On-line boosting is a technique for training information classifiers that has a wide applicability in machine learning. On-line boosting algorithms, in general, use one or more selectors to generate an initial classifier (e.g., a strong learner) by linearly combining a set of weak learners. Once the initial classifier is generated, subsequent samples are presented one-by-one, or in batches, to the selectors and classified using weak learners that are part of each selector. The weak learners are determined to misclassify the sample are penalized by having their error rates increased, whereas the weak learners that are determined to classify the sample correctly are rewarded by having their error rates reduced. After penalties and rewards are administered, the weak learner from each selector that has the best (e.g., lowest) error rate may be included (or allowed to remain) in the classifier. In that regard, the greater the penalty on a weak learner, the less likely that the weak learner will be subsequently included in the classifier.

When training data includes an imbalanced number of positive and negative samples, an asymmetric learning approach may be used. In asymmetric learning, weak learners are penalized differently based on the types of errors they make. For example, one asymmetric learning approach is disclosed in Viola, P., Jones, M., "*Fast and robust classification using asymmetric AdaBoost and a detector cascade*" Advances in Neural Information Processing Systems, vol. 14, pp. 1311-1318 (2002), which is hereby incorporated by reference herein in its entirety. According to this approach, weak learners are penalized k times more when they generate false-negatives than when they generate false-positives. The value of k is determined heuristically and remains unchanged for the period during which a classifier is trained (i.e., k is static).

According to some embodiments, mechanisms for training information classifiers are presented where weak learners are penalized based on a dynamic asymmetric loss criterion. The asymmetric loss criterion is based on a count of data samples (e.g., images) that have already been exposed to the system and is re-calculated every time a new sample arrives at the system. Under this approach, when a weak learner misclassifies a sample, that weak learner is penalized depending on how many samples have so far been used in training the classifier. In some embodiments, the asymmetric loss criterion may reflect the ratio of positive and negative samples within a training data set. As that ratio shifts with the introduction of new samples, the asymmetric loss criterion may change dynamically to either increase or decrease the penalty applied to weak learners when they misclassify a sample.

Furthermore, according to some embodiments, mechanisms for training information classifiers are presented that adjust the importance weight accorded to a newly arrived sample based on the numbers of positive and/or negative samples exposed to the mechanism prior to the arrival of the sample. Adjusting the importance weight in this manner may be useful in situations where computed tomography (CT) angiogram images are classified to detect anatomical structures, such as the carina, the pulmonary trunk, and the aortic arch. In such applications, one patient data set may include at most hundreds of positive images of the desired structures that are dispersed among millions of negative samples. In such circumstances where positive samples are harder to come across, according a greater importance weight to those samples may be desirable.

FIG. 1 illustrates an example of a system 100 that performs classification in accordance with some embodiments. In some embodiments, system 100 can be a computer aided detection system. As illustrated, input image 102 (such as a medical imaging image of an anatomic structure) can be received and provided to detector 104. Detector 104 can be a system including a hardware processor that implements a linear classifier F(x). The linear classifier F(x) may be of the form:

$$F(x) = \text{sign}\{\Sigma_{j \in \Phi} \alpha_j \times h_j(x)\}, \quad (1)$$

where $h_j(x)$ is an output returned by $j^{th}$ weak learner for image x 102, $\alpha_j$ is a voting weight of the $j^{th}$ weak learner, and $\Phi$ denotes the set containing the indices of selected weak learners. This linear classifier can have been configured to detect a certain anatomic structure in input image 102 by having been "trained" as described herein. The classifier can then output a "1" if the sample contains the desired certain anatomic structure, otherwise it can return a "−1".

Because anatomic structures may appear at different scales, the detector may perform a multi-scale search to locate the anatomic structures.

Figure 8:
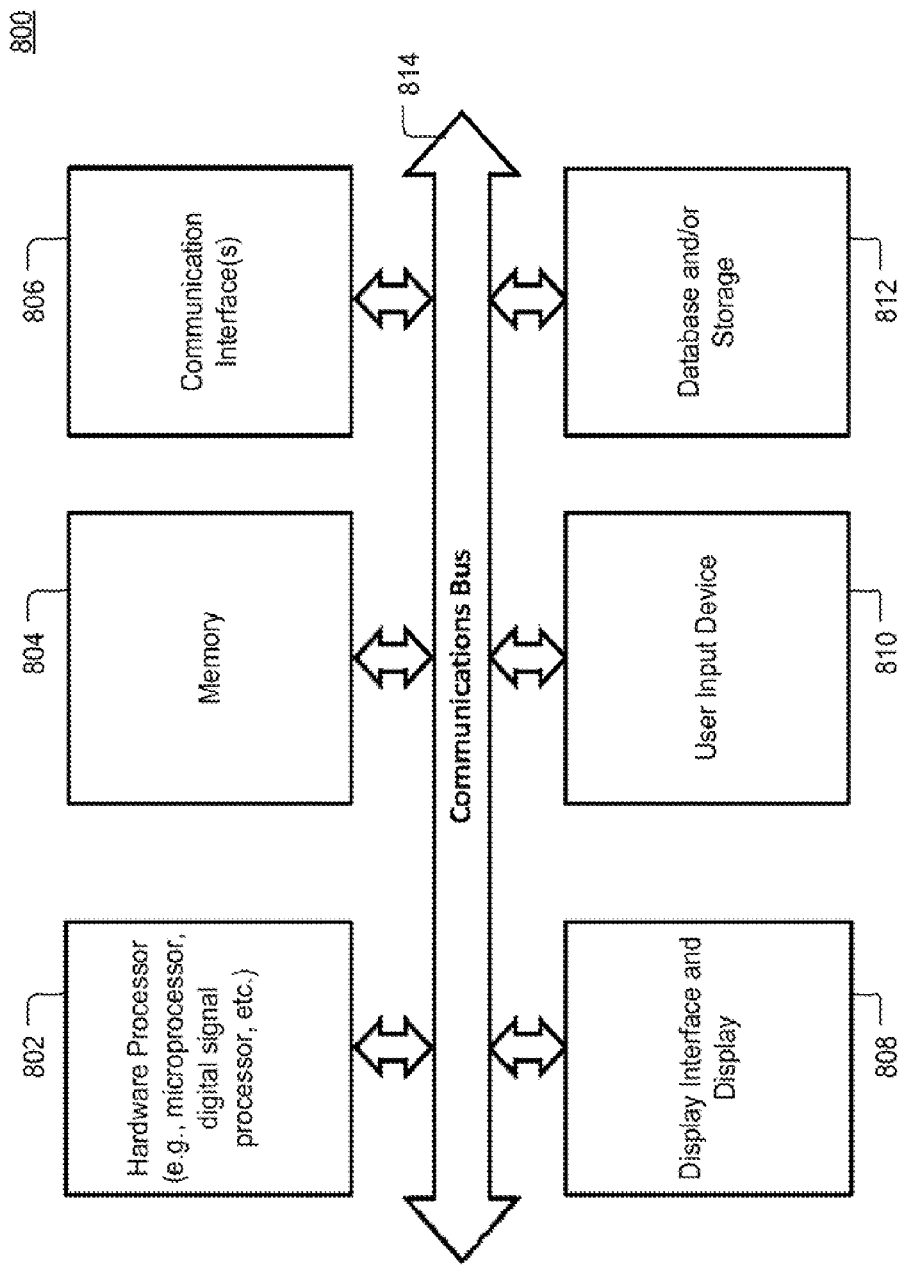
FIG. 8 is a block diagram of an example of hardware for a system for classifying images in accordance with some embodiments of the disclosed subject matter.

Image 102 and its classification (i.e., "1" or "−1") can then by reviewed by verifier 106. Verifier 106 can be any suitable mechanism for authoritatively determining whether image 102 was classified correctly by detector 104 and for specifying a "ground truth" for a desired object (i.e., a true location for the desired object). For example, verifier 106 can be a device through which a radiologist inspects the image and determines whether the certain anatomic structure is in fact present and therefore whether the classification is correct. Images that are correctly classified by detector 104 can be output at images 108. Images that are incorrectly classified by detector 104 can be output as images 110. Images 110 can include the authoritative classification information (i.e., information that indicates at least one of a true-positive, true-negative, false-positive, and false-negative classification of the images) and the images and information can be provided to updater 112 for updating the linear classifier in detector 104. Updater 112 can update the linear classifier in any suitable manner, such as that described herein in connection with FIGS. 2 and 3. As is discussed in further detail with respect to FIG. 8, updater 112 may include a memory and a hardware processor that is configured to execute any process (or part thereof) for updating the linear classifier, such as that discussed in connection with FIGS. 2-7.

In accordance with some embodiments, these mechanisms can be used for automatic detection of anatomic structures using on-line boosting. For example, in some embodiments, these mechanisms can be used to detect a human pulmonary trunk, a human carina, and a human aortic arch.

Although system 100 and the mechanisms of FIGS. 2-7 are described herein in the context of detection of anatomic structures in medical imaging images, it should be apparent to one of ordinary skill in the art that this is just an example of an application of this technology and that this technology can be used for any suitable application. For example, in some embodiments, this technology can be used to classify and/or perform detection in any suitable image or in any suitable data, can be used for real-time object detection and/or real-time object tracking, can be used for intelligent video surveillance, content based image retrieval, face and activity recognition, traffic control, and human-computer interfaces, etc.

Figure 2:
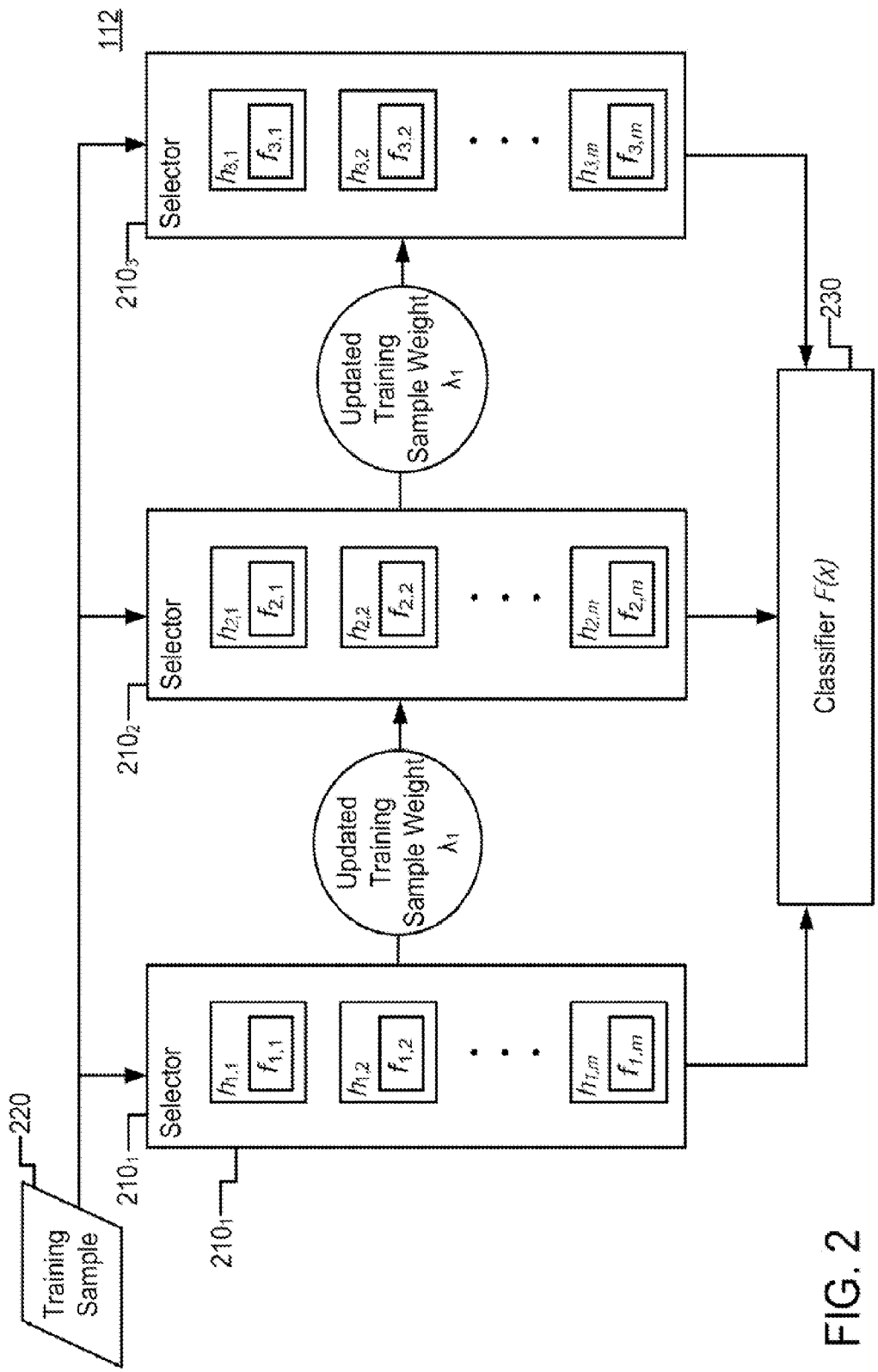
FIG. 2 is a block diagram of an example of a component of the system of FIG. 1.

Turning to FIG. 2 a diagram of the logic structure of updater 112 in accordance with some embodiments is shown. As illustrated, updater 112 includes selectors $210_n$, where $n \in \{1, 2, 3\}$. Each of selectors $201_n$, includes a pool of features $F_n$ to be used for classification and a set of weak learners $H_n$ corresponding to the features in the pool. Any suitable weak learner can be used in some embodiments. For example, in some embodiments, a weak learner can be implemented using a decision stump that compares a feature value for a sample and the feature to a threshold for the feature that is dynamically set.

Any suitable features can be used in some embodiments. For example, in some embodiments, 2D Haar patterns can be used as features for classification. More particularly, for example, in some embodiments, four 2D Haar patterns at different positions, scales, and aspect ratios (and/or any other variations) can be used to form an initial set of features, and, from this set, any suitable number of features can be randomly selected to form a pool of features. As another example, in some embodiments, 3D Haar patterns, local binary patterns (LBP), histogram of gradients (HOG), SIFT, or any other suitable patterns, can be used.

In operation, each selector $210_n$ receives a sample 220 and classifies the sample with the weak learners $h_{n,m}$ in its corresponding set of weak learners $H_n$ (where index m denotes a position of a weak learner in the set $H_n$). Afterwards, selector $210_n$ updates an associated error rate for each of the weak learners $h_{n,m}$ based on the classification, selects one of the weak learners $h_{n,m}$ as a best weak learner, and updates classifier 230 based on parameters of the selected best weak learner.

In some embodiments, selectors $210_n$ may be executed sequentially. That is, selector $210_1$ may be executed first, selector $210_2$ may be executed after the execution of selector $210_1$ is completed, and selector $210_3$ may be executed after the execution of selector $220_2$ is finished. Upon execution, each selector 210 may update an importance weight for sample 220 and pass the updated weight onto the next selector $210_{n+1}$ in the sequence. The next selector $210_{n+1}$ may then use the updated weight to calculate the error rates for the weak learners in the corresponding weak learner set $H_{n+1}$. Furthermore, the next selector $210_{n+1}$ may also update the importance weight for sample 220 and pass the updated importance weight further to the selector after it (selector $210_{n+2}$) in the sequence. In other words, at least some of selectors $210_n$ may use an importance weight for the sample that has been determined by another of selectors $210_n$.

Although in this example, updater 112 includes three selectors, in other examples it may include any number of selectors (e.g., a single selector, five selectors, or ten selectors). Furthermore, although in this example each of selectors $210_n$ includes the same set of features as the other selectors $210_n$, in other examples the selectors 210 may include different sets of features. For instance, selectors $210_1$ and $210_2$ may include different numbers and/or types of features from one another. In that regard, selectors $210_1$ and $210_2$ may also include different numbers and/or types of weak learners. Updater 112, in other words, is not limited to any number and/or type of weak learners, features, or selectors that it can include.

Figure 3:
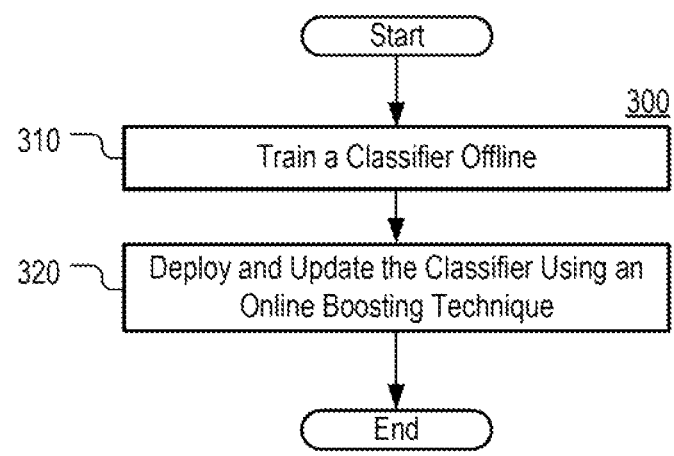
FIG. 3 is a flow diagram of an example of a process for updating a classifier in accordance with some embodiments of the disclosed subject matter.

FIG. 3 is a flowchart of an example of a process 300 for training a classifier in accordance with some embodiments. At 310, the classifier F(x) is trained offline using a boosting technique. The classifier may be trained based on one or more sets of weak learners and a set of training data. At 320, the classifier F(x) is deployed and updated using an on-line boosting process. As discussed above, in some embodiments, the classifier may be a medical image classifier that is trained to recognize depictions of anatomical structures, such as the carina or the aortic arc. In other embodiments, however, the classifier may be an image classifier that is configured to recognize other types of images (e.g., images of faces, license plates, etc.).

Figure 4:
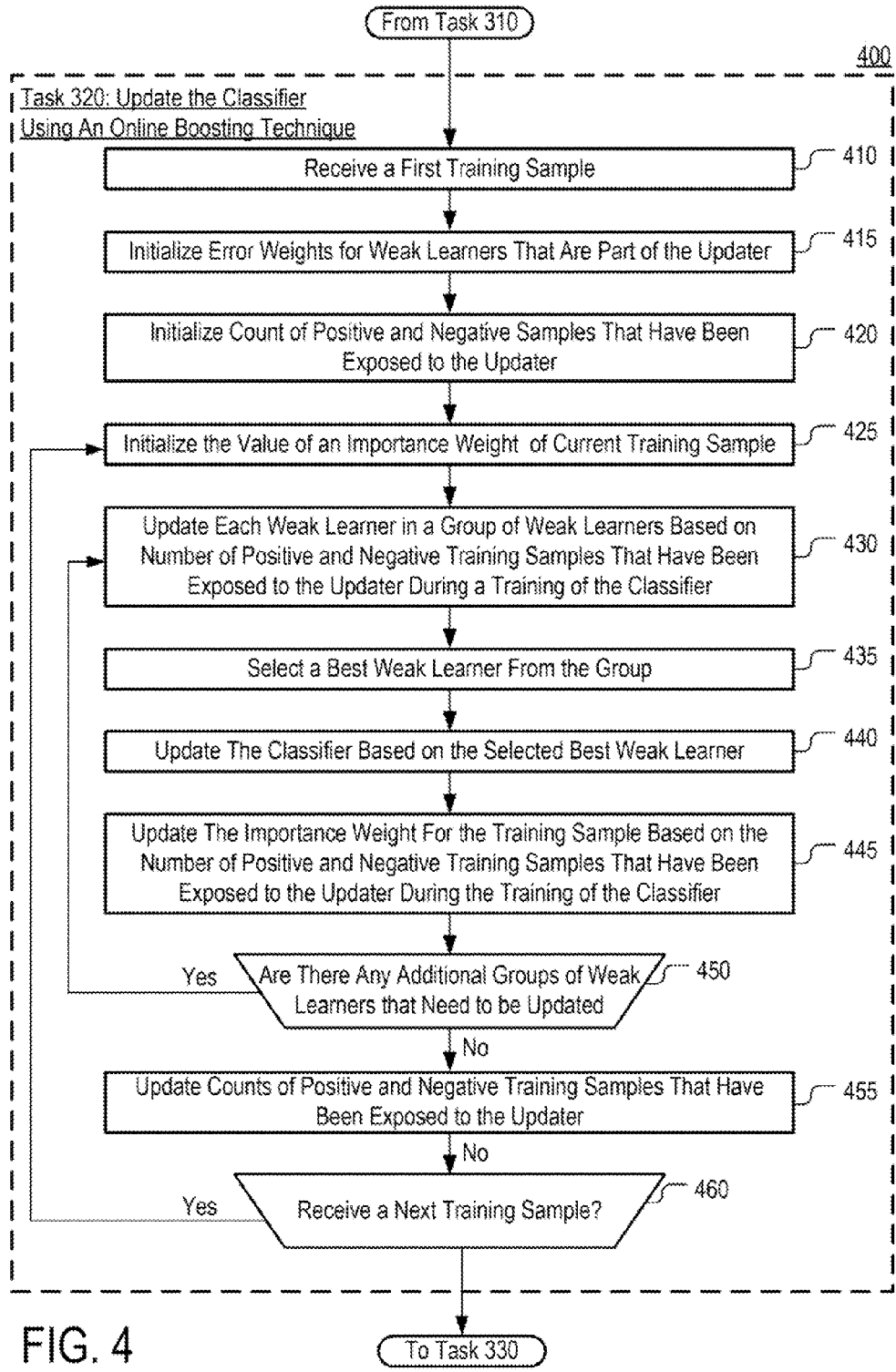
FIG. 4 is a flow diagram of an example of a process associated with the process of FIG. 3 in accordance with some embodiments of the disclosed subject matter.

FIG. 4 is a flowchart of an example of process 400 for updating a classifier by using an on-line boosting technique as specified by step 320 of FIG. 3. As noted, in some embodiments, process 400 may be executed by updater 112. During the execution, samples (or frames of samples) may be received in a sequence and used to gradually update the classifier F(x). Samples that depict a feature of interest that the classifier F(x) is trained to recognize (e.g., the carina or the aortic arc) are considered to be positive samples, whereas samples that lack the feature are referred to as negative samples. The numbers of positive samples and negative samples that have been exposed to updater 112 may be counted. The counts of positive samples and/or negative samples may then be used in updating the classifier.

At 410, a first sample is received by process 400. In some embodiments, the sample may be an image. In some embodiments, the sample may be received as part of a training example (x, y) where x is the sample and the value of y indicates whether the sample depicts the feature of interest that the classifier is trained to recognize. For instance, if y=−1, this might indicate that the sample x lacks the feature of interest, while y=1 may indicate the opposite. In that regard, the value of y may be used to determine whether the sample x is a positive sample or a negative sample.

At 415, the error rate weights $\lambda_{n,m}^{TP}$, $\lambda_{n,m}^{FP}$, $\lambda_{n,m}^{TN}$, and $\lambda_{n,m}^{FN}$ for each weak learner m in a group of weak learners n are initialized (e.g., set to equal 1). As is further discussed below, in some embodiments, each weak learner is associated with such a set of error weights that are specific to that learner. These weights are subsequently used to calculate the error rate for the weak learner.

At 420, the values $num^{pos}$ and $num^{neg}$ are initialized. The value $num^{pos}$ indicates the number of positive samples that have been exposed to updater 112 during a training of the classifier F(x). Similarly, the value $num^{neg}$ indicates the number of negative samples that have been exposed to the updater during the training of the classifier. Together, in some embodiments, the combination of $num^{pos}$ and $num^{neg}$ may indicate the total count of samples that have been used during the training of the classifier. In this example, $num^{pos}$ and num$^{neg}$ are numbers (e.g., integers), but in other examples they may be alphanumeric strings or any other type of indication.

In some embodiments, the values of num$^{pos}$ and num$^{neg}$ may be based on the counts of the positive and negative samples, respectively, that are used to train the classifier F(x) at 310 (e.g., prior to the beginning of the on-line boosting). Furthermore, in some embodiments, the values of num$^{pos}$ and num$^{neg}$ may be based only on samples that have been used during the on-line updating of the classifier (e.g., during the execution of step 320). Furthermore, in some embodiments, the values of num$^{pos}$ and num$^{neg}$ may be based on samples that have been used during either one of the initial training of the classifier (e.g., during the execution of step 310) and the on-line updating of the classifier (e.g., during the execution of step 320).

In this example, the values of num$^{pos}$ and /or num$^{neg}$ are set at 420 to an initial value of 1 and subsequently updated to reflect whether a given sample is positive or negative (step 455) only after the classifier has been updated based on that sample. In that regard, in this example, the value of num$^{pos}$ indicates the number of positive samples exposed to the system executing process 400 during that process's execution (e.g., number of positive samples that have been used to train the classifier prior to the receipt of the sample that is currently processed by process 400). Similarly, in this example, the value of num$^{neg}$ indicates the number of negative samples exposed to the system executing process 400 during that process's execution (e.g., number of negative samples that have been used to train the classifier prior to the receipt of the sample that is currently processed by process 400). In other examples, however, the values of num$^{pos}$ or num$^{neg}$ may be updated to reflect whether the sample received at 410 is positive or negative before that sample is used to update the classifier.

At 425, an importance weight λ for the sample x is set to an initial value (e.g., set to equal 1). At 430, the error rate for each weak learner m in a group of weak learners n is updated based on at least one of the importance weight λ of the sample and one of the error rate weights $\lambda_{n,m}^{TP}$, $\lambda_{n,m}^{FP}$, $\lambda_{n,m}^{TN}$, and $\lambda_{n,m}^{FN}$ for that weak learner. At 435, the best weak learner in the group n is selected based on the updated error rates (e.g., the weak learner with the lowest error rate may be selected). At 440, the classifier is updated. In some embodiments, updating the classifier may include replacing a weak learner that is part of the classifier F(x) with the best weak learner. Furthermore, in some embodiments, updating the classifier may include changing the voting weight of a weak learner that is already part of the classifier F(x). At 445, the importance weight λ of the sample that is currently being processed is updated. At 450, process 400 determines whether there are other groups of weak learners that need to be updated based on the sample. If there are other groups of weak learners that need to be updated, steps 430-445 are executed for a next group of weak learners. Each iteration of steps 430-445 may correspond to the actions performed by a different one of selectors 200 as discussed with respect to FIG. 2.

At 455, one of the values num$^{pos}$ and num$^{pos}$ is updated based on whether the sample that was just processed at steps 430-455 is a positive sample or a negative sample. In some embodiments, if the sample is positive, num$^{pos}$ is incremented by one and num$^{neg}$ is left unchanged. Otherwise, if the raining sample is negative, num$^{neg}$ is incremented by one and num$^{pos}$ is left unchanged. At 460, a next sample is received and process 400 returns to 425 where the value of the importance weight λ for the current sample (e.g., the next sample) is reset (e.g., set to 1). Once the importance weight for the next sample is initialized, steps 430-455 are repeated for the next sample. Steps 420-450 may be repeated for as long as new samples continue to arrive at the system executing process 400 or until some other condition is met.

Figure 5:
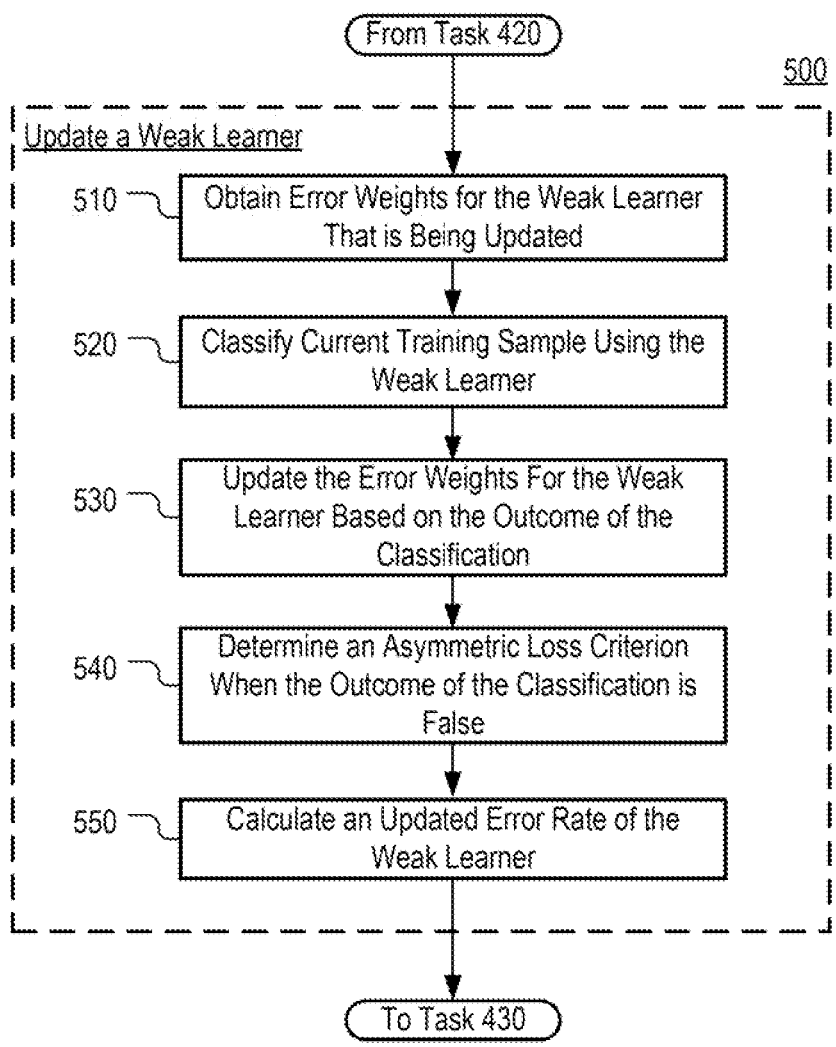
FIG. 5 is a flow diagram of an example of a process associated with the process of FIG. 3 in accordance with some embodiments of the disclosed subject matter.

FIG. 5 is a flowchart of an example of a process 500 for updating the error rate of a weak learner m (from a group of weak learners n) based on a received sample. In some embodiments, process 500 is executed once for each weak learner that is updated at 430 of FIG. 4.

At 510, at least one of the error weights $\lambda_{n,m}^{TP}$, $\lambda_{n,m}^{FP}$, $\lambda_{n,m}^{TN}$, and $\lambda_{n,m}^{FN}$ for the weak learner that is updated is obtained. At 520, the received sample is classified by the weak learner. The outcome of the classification may be one of a true-positive outcome (TP), a true-negative outcome (TN), a false-positive outcome (FP), and a false-negative outcome (FN). A true-positive outcome occurs when the sample includes the feature of interest that the classifier is trained to recognize and the weak learner correctly classifies the sample as including that feature. A true-negative outcome (TN) occurs when the sample lacks the feature of interest and the weak learner correctly classifies the sample as lacking the feature of interest. A false-positive outcome (FP) occurs when the sample lacks the feature of interest and the weak learner erroneously classifies the sample as including this feature. A false-negative outcome (FN) occurs when the sample includes the feature of interest and the weak learner classifies the sample as lacking the feature.

At 530, at least one of the error weights obtained at 510 is updated based on the classification. More specifically, if the outcome is true-positive (TP), the error weight $\lambda_{n,m}^{TP}$ is incremented by the importance weight λ of the sample. If the outcome is true-negative (TN), the error weight $\lambda_{n,m}^{TN}$ is incremented by the importance weight λ of the sample. If the outcome is false-positive (FP), the error weight $\lambda_{n,m}^{FP}$ is incremented by the importance weight λ of the sample. If the outcome is false-negative (FN), the error weight $\lambda_{n,m}^{FN}$ is incremented by the importance weight λ of the sample.

Step 540, in some embodiments, is executed only when the outcome of the classification at 520 is false-positive (FP) or false-negative (FN). At 540, an asymmetric loss penalty is determined for the weak learner. The asymmetric loss penalty is determined in accordance with an asymmetric loss criterion that is based on at least one of the count of positive samples num$^{pos}$ and the count of negative samples num$^{neg}$ that have been exposed during the training of the classifier. In some embodiments, the asymmetric loss criterion (ε) can have the form:

$$\varepsilon = \frac{1}{2+\epsilon}[Penalty^{FN} + Penalty^{FN}] \quad (2)$$

$$Penalty^{FP} = \left(\frac{num^{pos}}{num^{pos} + num^{neg}} + \epsilon\right) * \frac{\lambda^{FP}}{\lambda^{TP} + \lambda^{FP} + \lambda^{TN} + \lambda^{FN}} \quad (3)$$

$$Penalty^{FN} = \left(\frac{num^{neg}}{num^{pos} + num^{neg}} + \epsilon\right) * \frac{\lambda^{FN}}{\lambda^{TP} + \lambda^{FP} + \lambda^{TN} + \lambda^{FN}} \quad (4)$$

where Penalty$^{FP}$ is a penalty that is applied to the weak learner when the outcome of the classification of the sample is false-positive (FP), Penalty$^{FN}$ is a penalty that is applied to the weak learner when the outcome of the classification of the sample is false-negative (FN), ε is a smoothing factor, and $\lambda^{TP}$, $\lambda^{FP}$, $\lambda^{TN}$ and $\lambda^{FN}$ are the error weights for the weak learner whose error rate is being updated by process 500.

At 550, an updated error rate for the weak learner is re-calculated to take into account the classification of the received sample that is performed at 520. The error rate may be any metric that is calculated based on whether the weak learner has classified at least one sample correctly, and that is used, at least partially, as a basis for determining whether to include the weak learner into the classifier F(x) or change a voting weight for the weak learner, if it is already part of the classifier F(x). In some embodiments, the error rate is recalculated based on at least one of the updated weights $\lambda_{n,m}^{TP}$, $\lambda_{n,m}^{FP}$, $\lambda_{n,m}^{TN}$, and $\lambda_{n,m}^{FN}$ for the weak learner. For example, if the outcome of the classification of the sample is true-positive (TP), the error rate for the weak learner may be decremented by an amount that is based on the weight $\lambda_{n,m}^{TP}$. If the outcome of the classification of the sample is false-positive (FP), the error rate for the weak learner may be incremented by an amount that is based on the weight $\lambda_{n,m}^{FP}$. If the outcome of the classification of the sample is false-negative (FN), the error rate for the weak learner may be incremented by an amount that is based on the weight $\lambda_{n,m}^{FN}$. If the outcome of the classification of the sample is true-negative (TN), the error rate for the weak learner may be decremented by an amount that is based on the weight $\lambda_{n,m}^{TN}$.

In instances where the outcome of the classification of the sample is false-negative or false-positive, one of the penalties Penalty$^{FP}$ and Penalty$^{FN}$ may also be applied. More particularly, Penalty$^{FP}$ may be applied when the outcome is false-positive (FP) and Penalty$^{FN}$ may be applied when the outcome is false-negative. By way of example, applying the penalties Penalty$^{FP}$ and Penalty$^{FN}$ may include incrementing the error rate for the weak learner by an amount that is based on one of Penalty$^{FP}$ and Penalty$^{FN}$, respectively.

Figure 6:
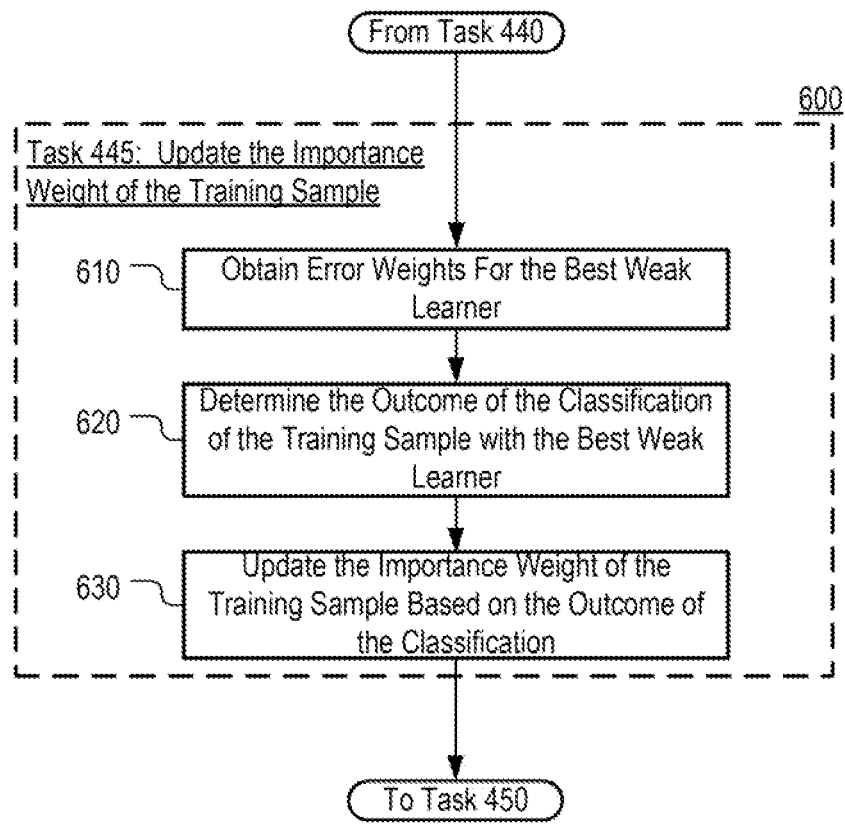
FIG. 6 is a flow diagram of an example of a process associated with the process of FIG. 3 in accordance with some embodiments of the disclosed subject matter.

FIG. 6 is a flowchart of an example of process 600 for updating the importance weight of a sample as specified by step 445 of FIG. 4. At 610, the error weights $\lambda_{n,best}^{TP}$, $\lambda_{n,best}^{FP}$, $\lambda_{n,best}^{TN}$, and $\lambda_{n,best}^{FN}$ for the best weak learner from group of weak learners n are obtained. As noted, the best weak learner is selected at 435 of FIG. 4. At 520, the outcome of the classification of the sample by the best weak learner is determined. At 530, the importance weight λ of the sample is updated based on the count of positive samples num$^{pos}$ and/or the count of negative samples num$^{neg}$ that have been exposed during the training of the classifier F(x). In some embodiments, the importance weight λ has the form:

$$\lambda = \frac{1}{2}\lambda\varphi\psi \quad (5)$$

$$\varphi = \frac{num^{pos} + num^{neg}}{\lambda_{n,best}^{TP} + \lambda_{n,best}^{FP} + \lambda_{n,best}^{TN} + \lambda_{n,best}^{FN}} \quad (6)$$

In some embodiments, the value of ψ may vary based on the outcome of the classification of the sample by the best weak learner. For example, if the outcome is true-positive (TP), Equation 7 may be used to determine ψ. If the outcome is false-negative (FN), Equation 8 may be used to determine ψ. If the outcome is true-negative (TN), Equation 9 may be used to determine ψ. And if the outcome is false-positive (FP), Equation 10 is used to determine ψ.

$$\psi = \frac{(\lambda_{n,best}^{TP} + \lambda_{n,best}^{FP})}{\lambda_{n,best}^{TP}}. \quad (7)$$

$$\psi = \frac{(\lambda_{n,best}^{TP} + \lambda_{n,best}^{FP})}{\lambda_{n,best}^{FN}}. \quad (8)$$

$$\psi = \frac{(\lambda_{n,best}^{TN} + \lambda_{n,best}^{FN})}{\lambda_{n,best}^{TN}}. \quad (9)$$

$$\psi = \frac{(\lambda_{n,best}^{TN} + \lambda_{n,best}^{FN})}{\lambda_{n,best}^{FP}}. \quad (10)$$

FIG. 7 shows an example of pseudo-code corresponding to portions of process 300 of FIG. 3 in accordance with some embodiments.

In accordance with some embodiments, any suitable hardware and/or software can be used to perform the mechanisms described herein (such as those illustrated in, and described in connection with, FIGS. 1-7). For example, a general purpose device such as a computer or a special purpose device such as a client, a server, etc. can be used to execute software for performing the mechanisms described herein. Any of these general or special purpose devices, such as device 800 of FIG. 8, can include any suitable components such as a hardware processor 802 (which can be a microprocessor, digital signal processor, a controller, etc.), memory 804, communication interface(s) 806, a display interface and display 808, user input devices 810, a database and/or storage 812, a communications bus 814, etc. Communications interface(s) 806 can enable the hardware and/or software to communicate with other communications networks (e.g., such as the Internet, wired networks, wireless networks, etc.), other equipment (e.g., such as medical scanning (e.g., such as a computed tomography scanner), diagnosis, display, etc. equipment), and/or any other suitable networks, devices, etc. This hardware and/or software can be implemented as part of other equipment (e.g., such as medical scanning (e.g., such as a computed tomography scanner), diagnosis, display, etc. equipment) or can be implemented as stand-alone equipment (which can be coupled to other equipment).

In some embodiments, any suitable computer readable media can be used for storing instructions for performing the processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any suitable media that is fleeting and devoid of any semblance of permanence during transmission, and/or any suitable intangible media.

Furthermore, it should be noted that FIGS. 3-7 are provided as examples only. At least some of the steps may be performed in a different order than represented, performed concurrently, or altogether omitted. Although in the processes of FIGS. 4-7 are described as being performed in an on-line fashion while the classifier is deployed, in other examples these processes may also be performed in a pseudo on-line fashion, where the classifies is trained before or after it is deployed. Although, the classifier discussed in the above examples is an image classifier, in other examples the classifier may be configured to recognize patterns in other types of data, such as audio data or trading data, for example. In that regard, the method and system for training classifiers is not limited to image classifiers only, but rather it can be used to train classifiers for recognizing patterns in other types of data.

As used herein, the term "image" may refer to multi-dimensional data composed of discrete image elements (e.g., pixels for two-dimensional images and voxels for three-dimensional images). The image may be, for example, a medical image of a subject collected using a computer tomography system, a magnetic resonance imaging system, an ultrasound imaging system, or any other medical imaging system or imaging modality known to one of skill in the art. The image may also be provided from non-medical contexts, such as, for example, remote sensing systems, electron microscopy systems, etc. The methods of the disclosed subject matter are not limited to such images, and can be applied to images of any dimension, e.g., a two-dimensional picture, a three-dimensional volume, or a four-dimensional space. For a two-dimensional or three-dimensional image, the domain of the image is typically a two-dimensional or three-dimensional rectangular array, where each pixel or voxel can be addressed with reference to a set of two or three mutually orthogonal axes.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims which follow. Features of the disclosed embodiments can be combined and rearranged in various ways.

What is claimed is:

1. A system for updating a classifier, comprising:
a hardware processor that is configured to:
receive a sample;
for each of a first plurality of weak learners, classify the sample using the weak learner, determine an outcome of the classification, and determine an updated error rate of the weak learner based on the outcome of the classification and at least one of:
(i) a count of positive samples used to update the classifier, and
(ii) a count of negative samples used to update the classifier;
select a first weak learner from the first plurality of weak learners based on the updated error rate of the first weak learner; and
update the classifier based on the first weak learner.

2. The system of claim 1, wherein the hardware processor is further configured to:
assign a first importance weight to the sample based on the outcome of the classification of the sample by the first weak learner and a count of samples that have been used to update the classifier;
for each of a second plurality of weak learners, classify the sample using the weak learner, determine an outcome of the classification, and determine an updated error rate of the weak learner based on the first importance weight;
select a second weak learner from the second plurality based on the updated error rate of the second weak learner; and
update the classifier based on the second weak learner.

3. The system of claim 2, wherein the first importance weight is determined based on a ratio between the count of positive samples and a count of all samples that have been used to update the classifier.

4. The system of claim 2, wherein the first importance weight is determined based on a ratio between the count of negative samples and a count of all samples that have been used to update the classifier.

5. The system if claim 1, wherein the classifier is a linear classifier having the form:

$$F(x)=\text{sign}\{\Sigma \alpha \times h(x)\},$$

where h(x) is an output returned by a weak learner h for a data sample x and $\alpha$ is a voting weight.

6. The system of claim 1, wherein each weak learner in the first plurality is based on different Haar feature.

7. The system of claim 1, wherein the count of positive samples includes a count of positive samples that have been used to update the classifier prior to the receipt of the sample.

8. A system for updating a classifier, comprising:
a hardware processor that is configured to:
receive a sample;
assign a first importance weight to the sample based on a count of samples used to update the classifier;
for each of a first plurality of weak learners, classify the sample using the weak learner, determine an outcome of the classification, and determine an updated error rate of the weak learner based on the outcome of the classification and the first importance weight;
select a first weak learner from the first plurality of weak learners based on the updated error rate of the first weak learner; and
update the classifier based on the first weak learner.

9. The system of claim 8, wherein the classifier is a linear classifier having the form:

$$F(x)=\text{sign}\{\Sigma \alpha \times h(x)\},$$

where h(x) is an output returned b a weak learner h for a data sample x and $\alpha$ is a voting weight.

10. The system of claim 8, wherein:
the first plurality of weak learners is associated with a first selector,
the first importance weight is determined by a second selector associated with a second plurality of weak learners,
the first importance weight is determined based on a classification of the sample by a second weak learner from the second plurality that is performed prior to the classification of the sample by the first weak learner from the first plurality, and
the first importance weight is used by the first selector to calculate error rates of weak learners from the first plurality.

11. The system of claim 8, wherein the first importance weight is determined based on a ratio between a ennui of negative samples used to update the classifier and a count of all samples used to update the classifier.

12. The system of claim 8, wherein the first importance weight is determined based on a ratio between a count of positive samples used to update the classifier and a count of all samples used to update the classifier.

13. The system of claim 8, wherein each weak learner in the first plurality is based on a different Haar feature.

14. The system of claim 8, wherein the sample is a medical imaging image.

15. A method for updating a classifier, comprising:
receiving a sample;
for each of a first plurality of weak learners, classifying the sample using the weak learner, determining an outcome of the classification, and determining, by a hardware processor, an updated error rate of the weak learner based on the outcome of the classification and at least one of:
(i) a count of positive samples used to update the classifier, and
(ii) a count of negative samples used to update the classifier;
selecting a first weak learner from the first plurality of weak learners based on the updated error rate of the first weak learner; and
updating the classifier based on the first weak learner.

16. The method of claim 15, further comprising:
assigning a first importance weight to the sample based on the outcome of the classification of the sample by the first weak learner and a count of samples used to update the classifier;
for each of a second plurality of weak learners, classifying the sample using the weak learner, determining an outcome of the classification, and determining an updated error rate of the weak learner based on the first importance weight;
selecting a second weak learner from the second plurality based on the updated error rate of the second weak learner; and
updating the classifier based on the second weak learner.

17. The method of claim 16, wherein the first importance weight is determined based on a ratio between the count of positive samples and a count of all samples used to update the classifier.

18. The method of claim 16, wherein the first importance weight is determined based on a ratio between the count of negative samples and a count of all samples used to update the classifier.

19. The method of claim 15, wherein the classifier is a linear classifier having the form:

$$F(x)=\text{sign}\{\Sigma\alpha\times h(x)\},$$

where h(x) is an output returned by a weak learner h for a data sample x and α is a voting weight.

20. The method of claim 15, wherein each weak learner in the first plurality is based on a different Haar feature.

21. The method of claim 15, wherein the count of positive samples used to update the classifier includes a count of positive samples that have been used to update the classifier prior to the receipt of the sample.

22. A method for updating a classifier, comprising:
receiving a sample;
assigning a first importance weight to the sample based on a count of samples used to update the classifier;
for each of a first plurality of weak learners, classifying the sample using the weak learner, determining an outcome of the classification, and determining, by a hardware processor, an updated error rate of the weak learner based on the outcome of the classification and the first importance weight;
selecting a first weak learner from the first plurality based on the updated error rate of the first weak learner; and
updating the classifier based on the first weak learner.

23. The method of claim 22, wherein the classifier is a linear classifier having the form:

$$F(x)=\text{sign}\{\Sigma\alpha\times h(x)\},$$

where h(x) is an output returned by a weak learner h for a data sample x and α is a voting weight.

24. The method of claim 22, wherein:
the first plurality of weak learners is associated with a first selector,
the first importance weight is determined by a second selector associated with a second plurality of weak learners,
the first importance weight is determined based on a classification of the sample by a second weak learner from the second plurality that is performed prior to the classification of the sample by the first weak learner from the first plurality, and
the first importance weight is used by the first selector to calculate error rates of weak learners from the first plurality.

25. The method of claim 22, wherein the first importance weight is determined based on a ratio between a count of negative samples used to update the classifier and a count of all samples used to update the classifier.

26. The method of claim 22, wherein the first importance weight is determined based on a ratio between a count of positive samples used to update the classifier and a count of all samples used to update the classifier.

27. The method of claim 22, wherein each weak learner in the first plurality is based on a different Haar feature.

28. The method of claim 22, wherein the sample is a medical imaging image.

29. A non-transitory computer-readable medium containing computer-executable instructions that, when executed by a processor, cause the processor to perform a method for updating a classifier, the method comprising:
receiving a sample;
for each of a first plurality of weak learners, classifying the sample using the weak learner, determining an outcome of the classification, and determining an updated error rate of the weak learner based on the outcome of the classification and at least one of:
(i) a count of positive samples used to update the classifier, and
(ii) a count of negative samples used to update the classifier;
selecting a first weak learner from the first plurality of weak learners based on the updated error rate of the first weak learner; and
updating the classifier based on the first weak learner.

30. The non-transitory computer-readable medium of claim 29, further comprising:
assigning a first importance weight to the sample based on the outcome of the classification of the sample by the first weak learner and a count of samples used to update the classifier;
for each of a second plurality of weak learners, classifying the sample using the weak learner, determining an outcome of the classification, and determining an updated error rate of the weak learner based on the first importance weight;
selecting a second weak learner from the second plurality based on the updated error rate of the second weak learner; and
updating the classifier based on the second weak learner.

31. The non-transitory computer-readable medium of claim 30, wherein the first importance weight is determined based on a ratio between the count of positive samples and a count of all samples used to update the classifier.

32. The non-transitory computer-readable medium of claim 30, wherein the first importance weight is determined based on a ratio between the count of negative samples and a count of all samples used to update the classifier.

33. The non-transitory computer-readable medium of claim 29, wherein the classifier is a linear classifier having the form:

$$F(x)=\text{sign}\{\Sigma\alpha\times h(x)\},$$

where h(x) is an output returned by a weak learner h for a data sample x and α is a voting weight.

34. The non-transitory computer-readable medium of claim 29, wherein each weak learner in the first plurality is based on a different Haar feature.

35. The non-transitory computer-readable medium of claim 29, wherein the count of positive samples used to update the classifier includes a count of positive samples that have been used to update the classifier prior to the receipt of the sample.

36. A non-transitory computer-readable medium containing computer-executable instructions that, when executed by a processor, cause the processor to perform a method for updating a classifier, the method comprising:
    receiving a sample;
    assigning a first importance weight to the sample based On a count of samples used to update the classifier;
    for each of a first plurality of weak learners, classifying the sample using the weak learner, determining an outcome of the classification, and determining, an updated error rate of the weak learner based on the outcome of classification and the first importance weight;
    selecting a first weak learner from the first plurality of weak learners based on the updated error rate of the first weak learner; and
    updating the classifier based on the first weak learner.

37. The non-transitory computer-readable medium of claim 36, wherein the classifier is a linear classifier having the form:

$$F(x)=\text{sign}\{\Sigma \alpha \times h(x)\},$$

where h(x) is an output returned by a weak learner h for a data sample x and α is a voting weight.

38. The non-transitory computer-readable medium of claim 36, wherein:
    the first plurality of weak learners is associated with a first selector,
    the first importance weight is determined by a second selector associated with a second plurality of weak learners,
    the first importance weight is determined based on a classification of the sample by a second weak learner from the second plurality that is performed prior to the classification of the sample by the first weak learner from the first plurality, and
    the first importance weight is used by the first selector to calculate error rates of weak learners from the first plurality.

39. The non-transitory computer-readable medium of claim 36, wherein the first importance weight is determined based on a ratio between a count of negative samples used to update the classifier and a count of all samples used to update the classifier.

40. The non-transitory computer-readable medium of claim 36, wherein the first importance weight is determined based on a ratio between a count of positive samples used to update the classifier and a count of all samples used to update the classifier.

41. The non-transitory computer-readable medium of claim 36, wherein each weak learner in the first plurality is based on a different Haar feature.

42. The non-transitory computer-readable medium of claim 36, wherein the sample is a medical imaging image.

* * * * *